United States Patent [19]

Bruchman et al.

[11] Patent Number: 5,258,040
[45] Date of Patent: Nov. 2, 1993

[54] PROSTHESIS FOR TENSILE LOAD-CARRYING TISSUE AND METHOD OF MANUFACTURE

[75] Inventors: William C. Bruchman; Carl W. Bolton; James R. Bain, all of Flagstaff, Ariz.

[73] Assignee: W. L. Gore & Associates, Newark, Del.

[21] Appl. No.: 662,184

[22] Filed: Feb. 28, 1991

Related U.S. Application Data

[60] Division of Ser. No. 568,625, Aug. 16, 1990, Pat. No. 5,049,155, which is a continuation of Ser. No. 732,811, May 10, 1985, which is a continuation of Ser. No. 415,565, Sep. 10, 1982, Pat. No. Des. 277,899.

[51] Int. Cl.$^5$ .......................... A61F 2/00; B60R 22/20
[52] U.S. Cl. ........................................ 623/66; 623/15; 57/201
[58] Field of Search ............... 57/210, 224, 21, 25, 57/26; 623/13, 66

[56] References Cited

U.S. PATENT DOCUMENTS

| | | |
|---|---|---|
| 2,271,173 | 1/1942 | Lay .......................... 57/21 |
| 3,176,316 | 4/1965 | Bodell . |
| 3,222,858 | 12/1965 | Gilmore et al. ................. 57/21 |
| 3,523,484 | 5/1970 | Hausner . |
| 3,545,008 | 12/1970 | Bader, Jr. . |
| 3,613,120 | 10/1971 | McFarland, Jr. ................ 623/13 |
| 3,805,300 | 4/1974 | Tascon-Alonso et al. . |
| 3,896,500 | 7/1975 | Rambert et al. . |
| 3,953,896 | 5/1976 | Treace . |
| 3,962,153 | 6/1976 | Gore . |
| 3,962,506 | 6/1976 | Dunahoo . |
| 3,971,670 | 7/1976 | Homsy . |
| 3,973,277 | 8/1976 | Semple et al. . |
| 3,987,497 | 10/1976 | Stoy et al. . |
| 3,988,783 | 11/1976 | Treace . |
| 3,992,725 | 11/1976 | Homsy . |
| 4,034,763 | 6/1977 | Frazier . |
| 4,118,532 | 10/1978 | Homsy . |
| 4,127,902 | 12/1978 | Homsy . |
| 4,129,470 | 12/1978 | Homsy . |
| 4,149,277 | 4/1979 | Bokros . |
| 4,208,745 | 4/1965 | Bodel . |
| 4,209,859 | 7/1980 | Hoffman . |
| 4,246,660 | 1/1981 | Wevers . |
| 4,248,924 | 2/1981 | Okita . |
| 4,255,820 | 3/1978 | Rothermel et al. . |
| 4,301,551 | 11/1981 | Dore et al. . |
| 4,329,743 | 5/1982 | Alexander et al. . |
| 4,354,339 | 8/1982 | Mueller et al. . |
| 4,400,833 | 8/1983 | Kurland . |
| 4,455,690 | 6/1984 | Homsy ......................... 623/13 |
| 4,569,190 | 2/1986 | Gilmore ....................... 57/21 |

FOREIGN PATENT DOCUMENTS

| | | |
|---|---|---|
| 2947743 | 5/1980 | Fed. Rep. of Germany . |
| 1305198 | 1/1973 | United Kingdom . |
| 2004835A | 4/1979 | United Kingdom . |
| 1602834 | 11/1981 | United Kingdom . |
| 2084468A | 4/1982 | United Kingdom . |

OTHER PUBLICATIONS

E. S. Grood et al., "Cruciate Ligament Prosthesis: Strength, Creep and Fatigue Properties", vol. 58-A, No. 8, The Journal of Bone and Joint Surgery, (Dec. 1976), pp. 1083-1088.

(List continued on next page.)

*Primary Examiner*—David Isabella
*Attorney, Agent, or Firm*—Finnegan, Henderson, Farabow, Garrett and Dunner

[57] ABSTRACT

The inventive article is a ligament or tendon prosthesis having multiple longitudinally parallel strands of microporous expanded polytetrafluoroethylene, the individual strands having an average porosity greater than 30% in the areas requiring tissue ingrowth. Additionally, strand dimensions and microstructure are selected so that tissue can penetrate throughout. The prosthesis is formed from multiple loops of a single continuous filament. Densified eyelets are formed in the loop for mounting to bone. The strands are twisted 180° or arranged in a loose braid about the prosthesis axis for improved load distribution during bending of the prosthesis.

9 Claims, 6 Drawing Sheets

OTHER PUBLICATIONS

H. W. Weavers, "The Specification and Design of a Substitute Mediocolateral Ligament", Med. Progr. Technol. 5, pp. 113–117.

Herzfeld, J., "The Technical Testing of Yarns and Textile Fabrics," 1898, pp. 76–107.

Danton, G., "The Theory and Practice of Seamanship," 1978, FIGS. 15.2, 15.7, 16.10 and 16.11.

Jenkins, D. H. R., et al., "The Role of Flexible Carbon-Fibre Implants as Tendon and Ligament Substitutes in Clinical Practice," Journal of Bone and Joint Surgery, vol. 62-B, No. 4, Nov. 1980, pp. 497–499.

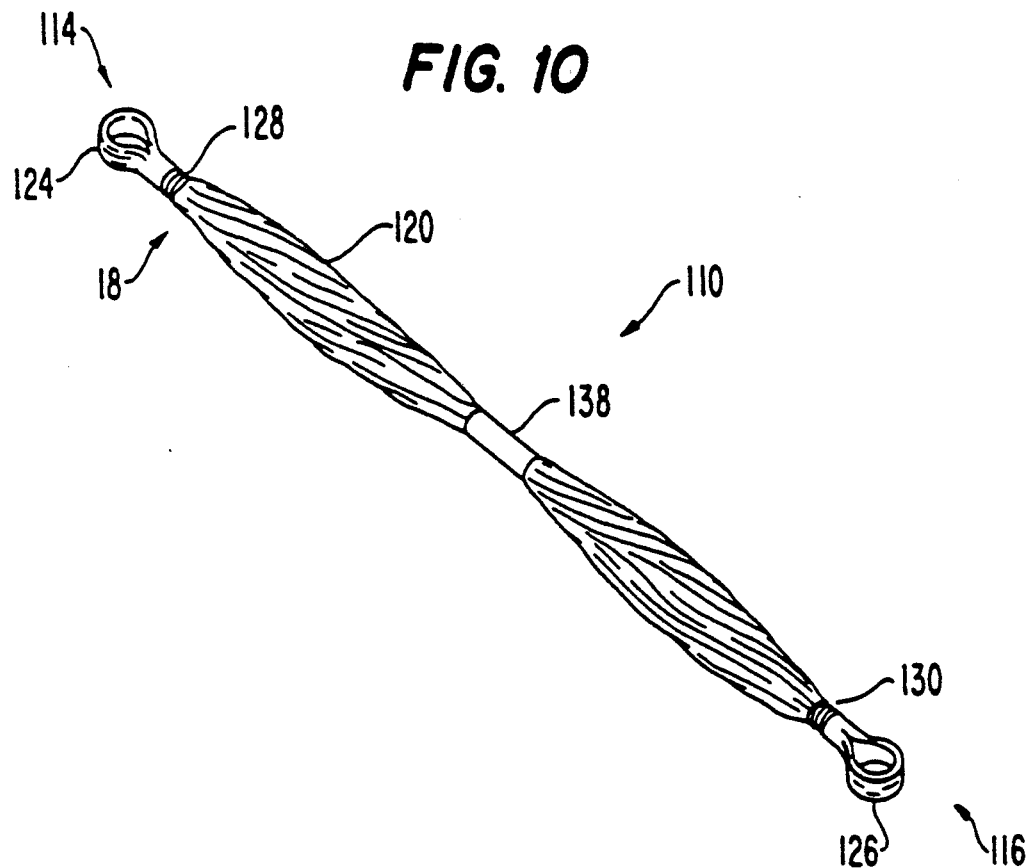
FIG. 10
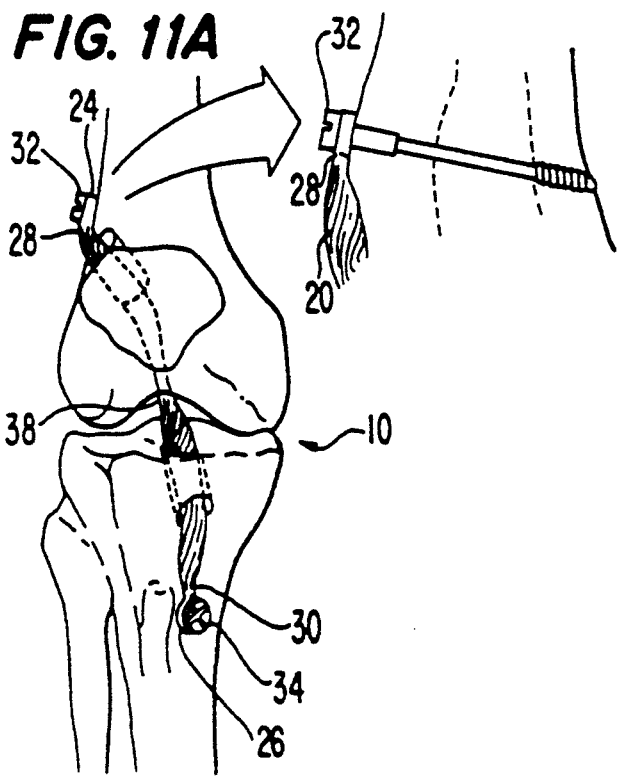
FIG. 11A
FIG. 11C
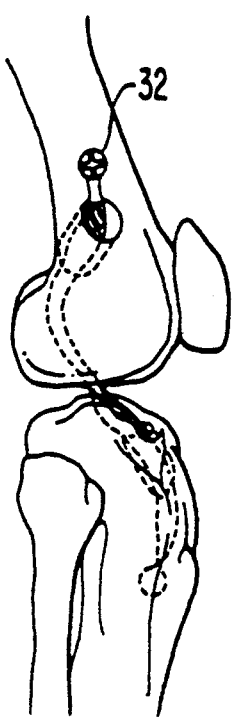
FIG. 11B

PROSTHESIS FOR TENSILE LOAD-CARRYING TISSUE AND METHOD OF MANUFACTURE

This is a division of application Ser. No. 07/568,625, filed Aug. 16, 1990 now U.S. Pat. No. 5,049,155, which was a continuation of Ser. No. 06/732,811 filed May 10, 1985, pending, which was a continuation of Ser. No. 06/415,565 filed Sep. 10, 1982 now U.S. Pat. No. Des. 277,899.

FIELD OF THE INVENTION

The inventive article described herein is a synthetic prosthesis for replacement or repair of ligaments or tendons.

DESCRIPTION OF THE PRIOR ART

The generally accepted method of repair of ligaments and tendons is through the use of tissue transplanted to the defect site from elsewhere in the body. This method of repair often fails due to a number of factors, including insufficient strength of the transplanted tissues, dependence of the transplanted tissue on revascularization for viability, and inadequate strength of attachment or fixation of the transplanted tissue.

A great need exists for a prosthetic device to replace damaged ligaments and tendons, and there have been a number of previous attempts at providing such devices. However, there is no prosthesis today which is widely accepted. Among the reasons for failure of prosthetic devices are inadequate tensile strength, lack of adequate fixation, deterioration of the device due to mechanical stresses, and deterioration of the prosthesis/tissue interface.

Previous method of attachment to bone and soft tissues which have been attempted include:

U.S. Pat. Nos. 3,971,670, 4,127,902, 4,129,470, 3,992,725, and 4,149,277. These patents teach attachment through tissue ingrowth into porous surfaces of the prosthetic device.

U.S. Pat. Nos. 3,613,120, 3,545,008, and 4,209,859. These patents teach methods of tissue attachment to porous fabrics with various methods of maintaining apposition to the repaired tissue.

U.S. Pat. Nos. 3,896,500, 3,953,896, 3,988,783, and 4,301,551. These patents teach attachment to bone by means of rigid mechanical devices such as screws, threads or other devices.

SUMMARY OF THE INVENTION

In accordance with the inventions, as broadly described herein, the prosthesis is made up of multiple porous strands of polytetrafluoroethylene (PTFE) formed from concentric loops of a continuous filament. Immediate postoperative attachment of the device is provided by integral eyelets formed from adhered, gathered loop ends, which can be affixed directly to bony tissue. This initial attachment is augmented and finally made redundant as tissue grows into the porous strand material providing permanent attachment of the prosthesis.

To achieve the foregoing objects and in accordance with the present invention, as broadly described herein, the method for making a tensile load-bearing tissue prosthesis of the type having a plurality of parallel longitudinally adjacent strands connected to at least one eyelet, the eyelet being for the initial attachment of the prosthesis to tensile force-applying bone tissue, comprises forming a plurality of elongated concentric loops from a continuous filament of the desired strand material until the desired number of parallel strands are obtained, the concentric loops defining a projected elongated area, and gathering the loop ends at one elongated area end to form the eyelet, the method including the step of securing the gathered loop ends against ungathering.

Preferably, the method includes the further steps of imparting a twist to the loop strands about the longitudinal axis of the prosthesis.

This invention will be further understood by reference to the drawings which are given for illustration only and are not intended to limit the scope of the invention but which are to be read in conjunction with the specifications.

BRIEF DESCRIPTION OF THE DRAWINGS

FIG. 10 depicts schematically a perspective view of yet another prosthesis constructed in accordance with the present invention; and FIGS. 11A, B, and C depict the implantation into a knee joint of the prosthesis of FIG. 8 into a knee joint as an anterior cruciate ligament prosthesis.

DESCRIPTION OF THE PREFERRED EMBODIMENTS

The inventive article described herein is a synthetic prosthesis for replacement or repair of ligaments or tendons. The prosthesis is made up of multiple strands of porous PTFE. The porosity of the strands is characterized by interconnecting void space throughout. Strand dimensions are small enough to permit tissue growth in and through the entire strand. The percent void space, or porosity, is greater than 30%, which allows mechanical attachment of tissue in the interstitial spaces of the prosthesis to provide sufficient attachment strength. This degree of porosity is a requirement only for those sections of the device which are intended to be anchored through tissue fixation. Porosity, as used here, is defined as;

$$\% \text{ Porosity} = \left[1 - \frac{\rho_2}{\rho_1}\right]100$$

where:

$\rho_2$ = density of porous material $\rho_1$ = density of solid PTFE making up the solid content of the porous material. For PTFE which has never been sintered $\rho_1 = 2.3$ gm/cm$^3$ and for materials which have been sintered a value of 2.2 gm/cm$^3$ is used for $\rho_1$, although this value can actually vary somewhat depending on sintering and cooling conditions.

Immediate postoperative attachment of the device is provided by eyelets which are attached directly to bony tissue. This initial attachment is augmented and finally made redundant as tissue grows into the porous strand material, providing permanent attachment of the prosthesis to tissue. Tissue can easily grow between and among the strands since they are not attached to each other nor held together tightly. However, the depth to which tissue can grow into each strand is governed by the dimensions of the interconnected void corridors or pathways through the porous microstructure. The complex intercommunicating void space is formed by the solid PTFE matrix. In some cases, the matrix is made up of large solid nodes interconnected by long flexible, relatively inelastic fibrils. Although the nodes may present rigid inflexible structures to ingrowing tissue, the fibrils can be bent and pushed aside by penetrating tissue. Other microstructures of this invention have much smaller nodes which appear merely as connection points for the fibrils. In both cases, the strength of the fibrils in tension is very high, and although they can be bent by tissue, they cannot be stretched significantly. The microstructures of this invention can be characterized by a mean interstitial dimension which can be used to predict the depth of tissue ingrowth. Short fibril lengths impede and bottleneck tissue invasion. Thus, for porous strands having short fibril lengths, the overall strand dimension must itself be small enough so that ingrowth and attachment will occur throughout the entire strand.

Figure 2:
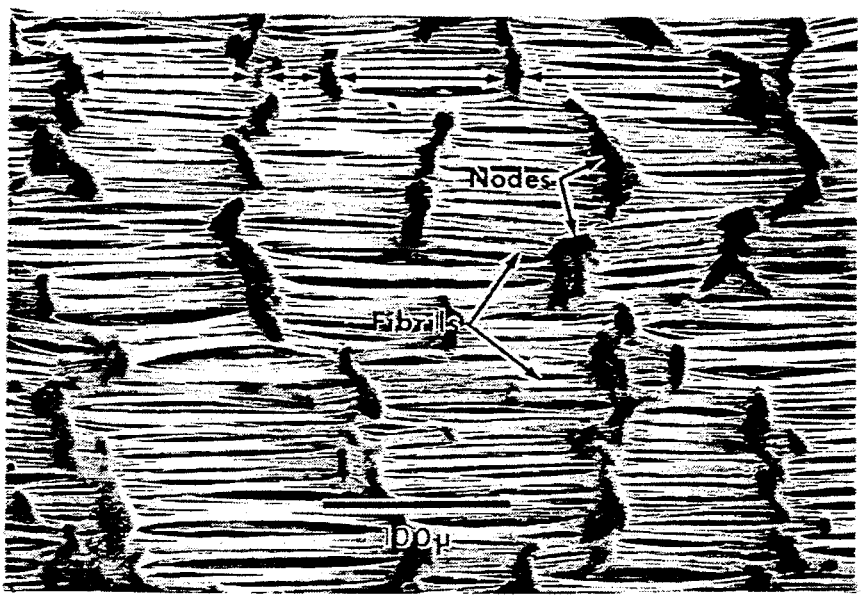
FIG. 2 is a photomicrograph of the PTFE material used in the construction of the prosthesis of Example B.

The methods used here to characterize the fibril length of a particular microstructure rely on visual examination of that microstructure. Photographs at a convenient magnification can be provided through scanning electron microscopy or, in some cases, light microscopy. The microporous PTFE materials of this invention can vary sufficiently in their microstructure so that different techniques of measuring the characteristic interstitial dimension must be used. Strand fibers such as those made by the process described in Example B possess a microstructure which can clearly be characterized by nodes interconnected by fibrils. The characteristic interstitial dimension for materials of this type can be determined through a direct measurement of the spacing between nodes. This measurement is taken along a line placed in the direction of strength orientation (FIG. 2). A large enough number of measurements must be taken so that the node spacing is adequately characterized. The mean node spacing thus provided is used to characterize the interstitial space and thereby predict the depth of ingrowth into that microstructure.

In strand material which has been manufactured by a stretching process such as is described in U.S. Pat. No. 3,962,153, or the products of U.S. Pat. No. 4,187,390, the nodes of PTFE can be smaller and much less defined. In highly stretched products made according to these patents, node spacing becomes very large and fibrils are packed together. The sintering step in production of these materials causes the bundles of fibrils to coalesce and form secondary attachment points. For this reason, the microstructure of such materials is not readily apparent even under magnification. In determining the characteristic interstitial dimension of these materials, it is necessary to measure the distance between fibril suspension points rather than measuring the fibril length (i.e., node spacing). The interstitial dimensions of these materials can be observed if samples are prepared for microscopy by slightly stretching the material at right angles to its direction of strength orientation. Upon stretching the sample 10% in the lateral direction, with the sample restrained from shrinking in the longitudinal direction, the points at which fibrils are connected become apparent under microscopic examination. The distance between fibril connections is then measured at all obvious gaps created between fibril bundles. This measurement is taken in the direction of strength orientation. As with the method described previously for node spacing, the number of measurements of fibril suspension distance must be sufficient to characterize interstitial dimensions of the microstructure.

Figure 4:
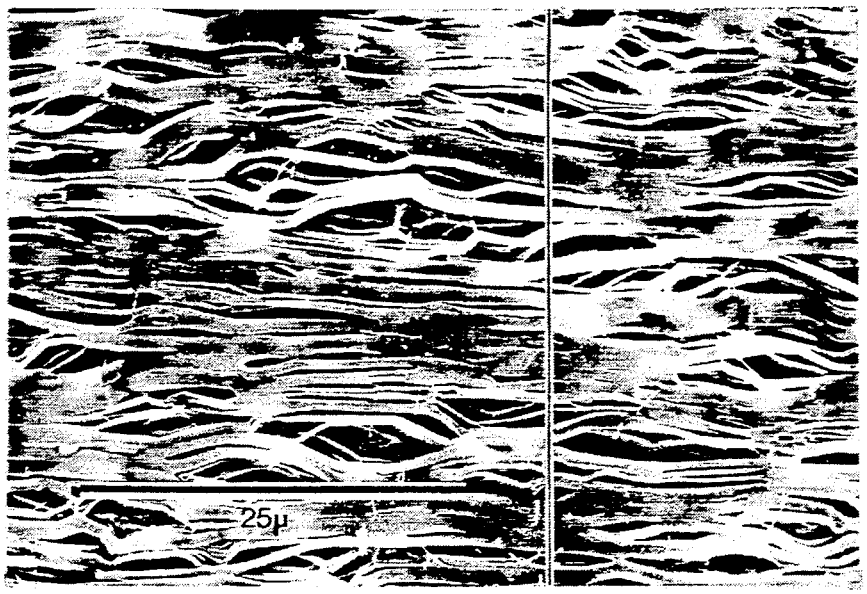
FIG. 4 is a photomicrograph of the material of FIG. 3 laterally stretched to provide for measurement of characteristic interstitial dimension.
Figure 1:
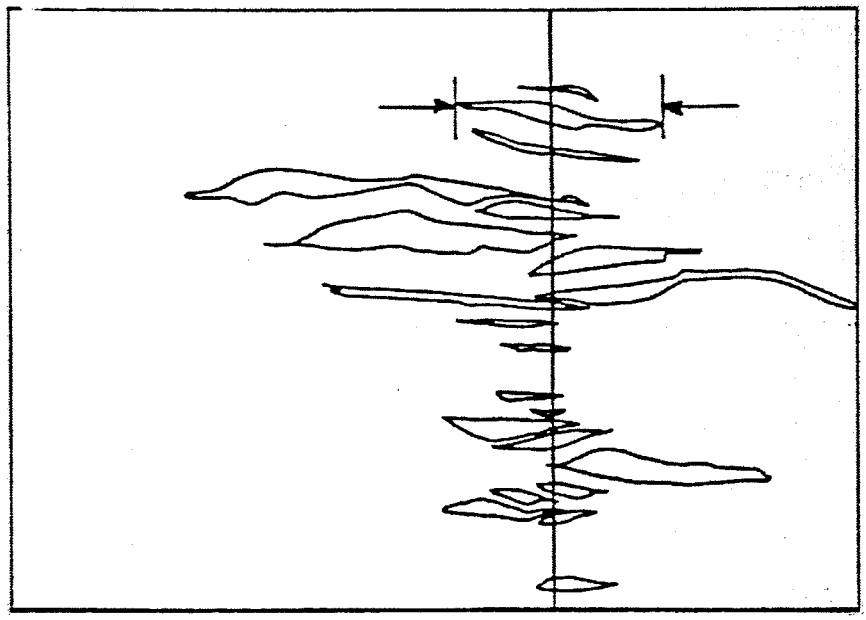
FIG. 1 is a schematic illustrating the procedure for measuring the characteristic interstitial dimension of the material in the photomicrograph in FIG. 4.
Figure 3:
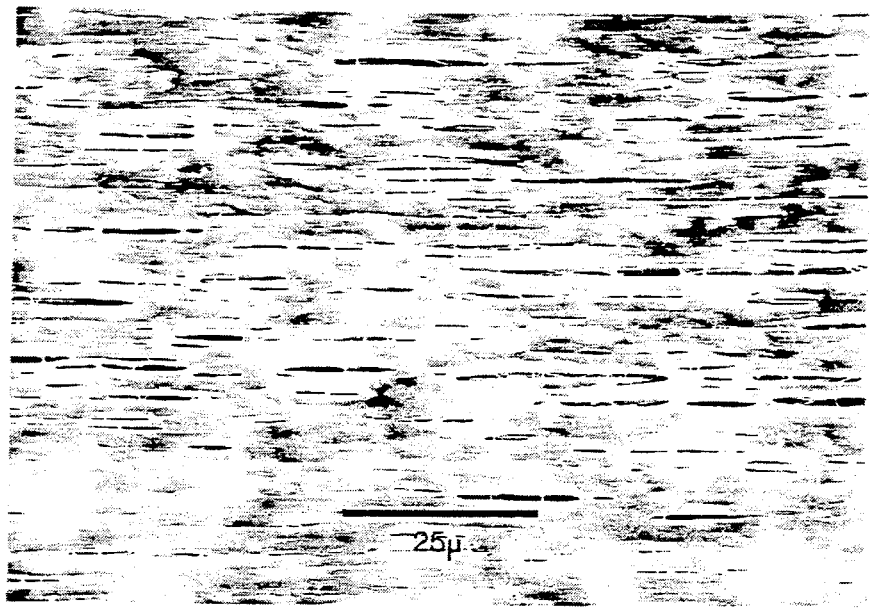
FIG. 3 is a photomicrograph of a PTFE material having nodes that are less well defined compared to the material in FIG. 2.

FIG. 3 shows how material of this type appears without lateral stretching as compared to FIG. 4 which is a micrograph of the same material with 10% lateral stretching. This lateral stretching, which is used only to characterize the microstructure of the material, represents a temporary structural reorientation. A force placed on the material in the longitudinal direction causes a return to the original lateral dimension and a restoration of the original microstructure. As previously described, it is believed that the fibrils composing this microstructure are pushed aside by ingrowing tissue. The method of measuring the characteristic interstitial dimension for materials of this type is shown in FIG. 1 relating to the photomicrograph of FIG. 4. Having once determined the characteristic interstitial dimension by the techniques described, the proper strand dimensions can be determined.

The maximum strand thickness which would allow tissue penetration through the entire strand is approximately two times the tissue penetration depth. The maximum strand thickness, as used here, refers to the appropriate minor cross-sectional dimension of a strand, e.g., the diameter of a strand of circular cross-section or the thickness of a strand or rectangular cross-section. In general, combinations of characteristic interstitial void dimension and strand thickness less than the maximum strand thickness are preferred because they allow complete tissue penetration across the strand cross-section in a shorter time interval.

A major requirement for a successful ligament or tendon prosthesis is that of adequate strength. In many situations prosthetic materials used to replace these natural structures are subjected to very high tensile loads. The strength of the prosthesis must in some cases by many times that of the peak load to which it will be exposed to compensate for the mechanical properties of the prosthesis which are time-dependent.

From a mechanical strength standpoint, one of ordinary skill in the art would realize that the number of individual strands needed for a particular application will depend on several factors. These include: the individual strand cross-sectional area; the tensile strength of the individual strand; and the tensile force requirement for that particular application, including any safety factors for creep strain limitations. The individual strands used in this invention can be constructed using the processes described in U.S. Pat. No. 3,953,566, U.S. Pat. No. 3,962,153 or following Example B. It is desirable to use a high matrix tensile strength material in order to minimize the overall physical dimensions of the device and thereby minimize the size of drill holes placed in the bone to mount the device. Matrix tensile strength refers to the strength of the polymer in a porous specimen and is used as defined in U.S. Pat. No. 3,953,566.

In the preferred form of this invention:
- The strand material is porous PTFE with a matrix tensile strength greater than 20,000 psi, a porosity greater than 30%, and a microstructure characterized by intercommunicating pathways formed by the boundaries of nodes and fibrils.
- Strand dimensions and characteristic interstitial dimensions of the microstructure are selected such that tissue ingrowth throughout the strand takes place in a rapid fashion.
- Each strand and the finished construction possess sufficient strength necessary to meet the mechanical requirements of the particular application.
- The parallel strands result from multiple loops formed from a continuous filament of the strand material.
- The ends of the multiple loops are gathered and formed into at least one eyelet for attaching the article to bone tissue.
- The uniformity of strand loading of the prosthesis under tensile force is enhanced through:
  1. Minimizing differences in loop length used to form the parallel strands.
  2. Compression of the loop strands in the eyelet segments to provide strand-to-strand adhesion.
- The prosthesis also includes means for distributing the tensile load among the strands as it passes around a radius, said means including:
  1. A twist in the strand bundle about its longitudinal axis.
  2. A loose strand braid.

Figure 5:
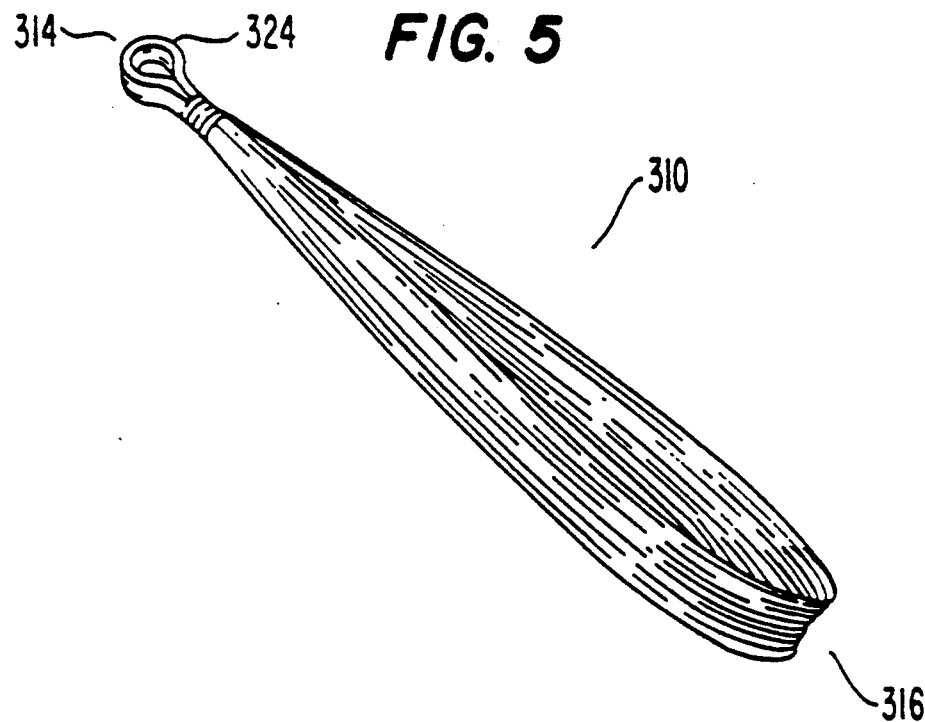
FIG. 5 shows a schematic perspective view of one prosthesis constructed in accordance with the present invention.

Although the ligament prosthesis embodiment in FIG. 10 is shown with a pair of opposing eyelets formed from elongated loops, the present invention also encompasses a single eyelet 324 formed in the loops gathered for attachment to bone. The loops at the other end 316 remain ungathered or splayed to provide attachment to soft tissue such as muscle tissue, as by suturing (see FIG. 5). In this latter case, the closed loop ends provide additional resistance to possible strand slippage past the sutures. The single eyelet embodiment of this prosthesis 310, could find use in the repair or replacement of tendons.

EXAMPLE A

This example demonstrates a prosthetic device which did not achieve satisfactory system strength because the strand thickness was too large for the interstitial dimension which characterized its microstructure (FIG. 1). The strand thickness (diameter) was 0.26 inches, porosity of the strand was approximately 80%, and the characteristic interstitial dimension was about 78 microns.

Figure 6:
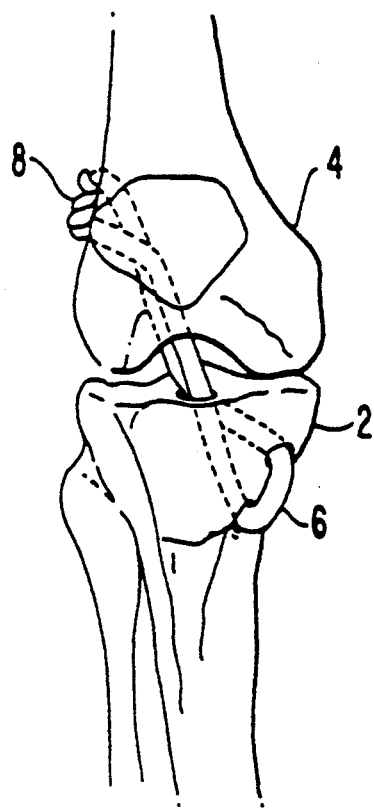
FIG. 6 depicts schematically the implantation of an anterior cruciate ligament prosthesis not constructed in accordance with the present invention.

This interstitial dimension was determined as shown in FIG. 2. The prosthesis was used to replace the anterior cruciate ligament of a dog by routing the material through drill holes in the tibia and femur. Four holes were drilled in the tibia 2 and femur 4 such that the prosthesis strand 6 formed a loop of material with two strands in the position of the original ligament (FIG. 6). Initial fixation was provided by tying the ends of the strand together in a knot 8 to form a continuous loop. Ingrowth and formation of tissue within the interstices of the microporous material were expected to augment the initial fixation strength and to distribute stresses to the surrounding tissue. Each of the strands crossing the knee joint possessed a tensile strength of about 550 pounds. The combined strength of these two strands was then 1,100 pounds. After having been implanted for 260 days, the knee joint was explanted.

Drill holes were placed in the tibia and femur for mounting into tensile test clamps. After removal of all supporting collateral structures about the knee, the femur was distracted from the tibia along the axis of the prosthetic ligament at a constant rate of 500 mm per minute until failure. The length spanning the intra-articular space between bone tunnels represented that portion of the prosthesis placed under tensile load during the test, due to tissue attachment to the prosthesis in the bone tunnels. The failure mode of the system was rupture of the prosthetic device at the level of exit from the bone tunnels. Surprisingly, this rupture took place at a value of only 200 lbs. Through histological inspection, we discovered that this reduction in strength was related to the restriction of bony ingrowth to generally less than 1 mm depth into the prosthesis. With a strand of this diameter and characteristic interstitial dimension, attachment takes place only at a circumferential ring of material on the periphery of the device. This reduced area then becomes the only load-bearing material of the prosthesis as a tensile force is initially applied. Failure occurs in this circumferential ring of material first and then progresses through the central portion of the prosthesis.

EXAMPLE B

The experience cited in Example A led to the discovery that tissue ingrowth must penetrate throughout the cross-section of the strand in order to provide adequate long-term system strength. Accordingly, a device was constructed using a strand of similar porosity and characteristic interstitial dimension but with a much smaller diameter. The strand material used to construct the anterior cruciate ligament prosthesis of this example was made as follows:

PTFE dispersion powder ("Fluon CD 123" resin produced by ICI America) was bended with 130 cc of "ISOPAR K" odorless solvent (produced by Exxon Corporation) per pound of PTFE, compressed into a pellet, and extruded into a 0.108 inch diameter rod in a ram extruder having a 96:1 reduction ratio in a cross-section from the pellet to the extruded rod.

The extruded rod still containing Isopar K was immersed in a container of Isopar K at 60° C. and stretched to 8.7 times its original length between capstans with an output velocity of about 86.4 ft/min. These capstans were about 2.8 inches in diameter with a center-to-center distance of about 4.5 inches. The diameter of the rod was reduced from about 0.108 inch to about 0.047 inch by this stretching. The Isopar K was then removed from this stretched material.

The stretched rod was then pulled through a circular densification die heated to 300° C. The opening in the die tapered at a 10° angle from about 0.050 inch to 0.025 inch and then was constant for about 0.025 inch length. The output velocity of the material exiting the die was 7.2 ft/min.

The stretched rod was then heated to 300° C. through contact with heated, driven capstans and stretched 4½ fold (350%) with an output velocity of 6.5 ft/min. These capstans had a diameter of 2.75 inches and a center-to-center distance of 4.5 inches.

Finally, the rod was restrained from shrinking and exposed to about 367° C. in an air oven for 30 seconds.

In the finished form, the fiber made with this process possessed the following characteristics:
Diameter=0.026 inches
Matrix Tensile Strength=74,000 psi
Porosity=80.8%
Characteristic Interstitial Dimension=74 μ

Figure 7:
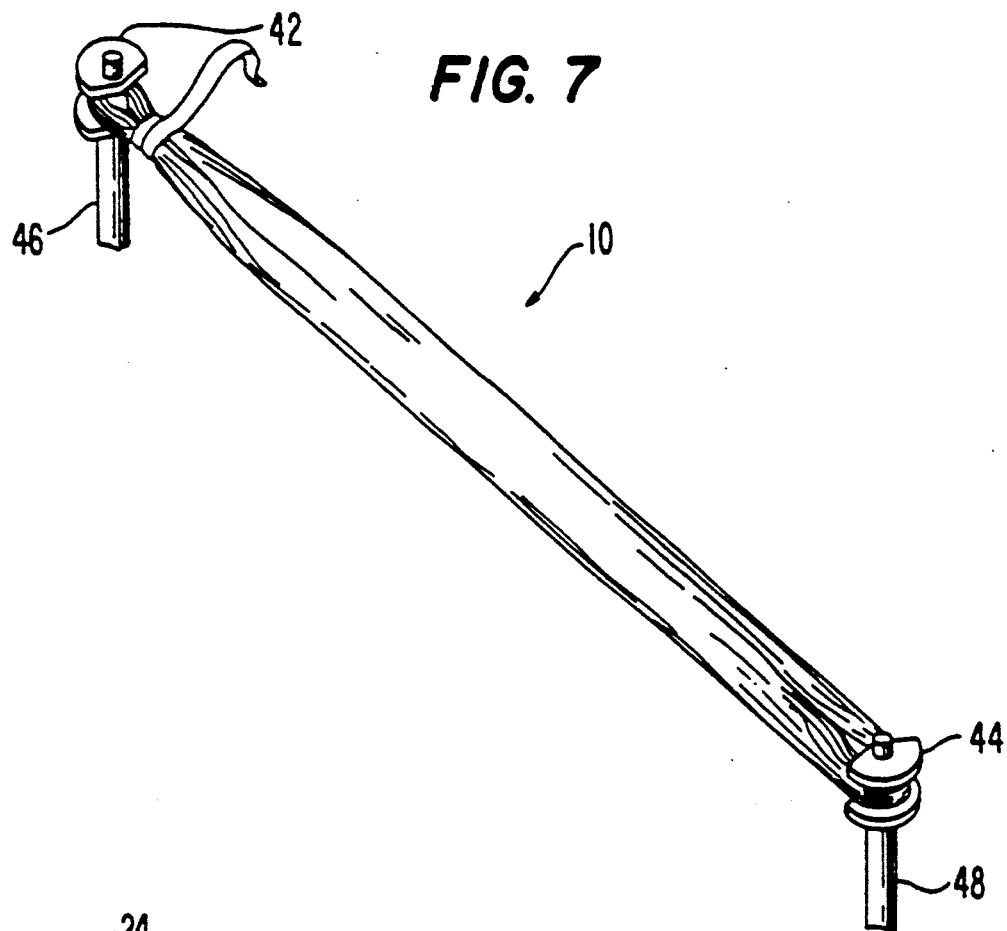
FIG. 7 depicts schematically a stage in one method of construction of a prosthesis of the present invention.

As illustrated in FIG. 7, prosthesis 10 was constructed on two steel spools 42, 44 which were mounted on a rack (not shown). The spools were supported on studs 46, 48 spaced 14 cm from center line to center line. These steel spools were threaded to allow demounting of one flange. The strand of PTFE material was passed around these two spools 80 times so that a total of 160 strands connected the two spools. The two free ends of the fiber were tied together with multiple square knots. One spool was demounted from the stud, rotated through 180° and remounted on the stud, thus imparting a one-half twist about the longitudinal axis of the construction. The construction was then wrapped with a thin film of PTFE a total of 25 revolutions each at three locations. This film was manufactured according to the teachings of U.S. Pat. No. 3,962,153 and had the following characteristics:
Width=0.375"
Thickness=0.0025"
Longitudinal matrix tensile strength=70,000 psi
Porosity=84%

Figure 8:
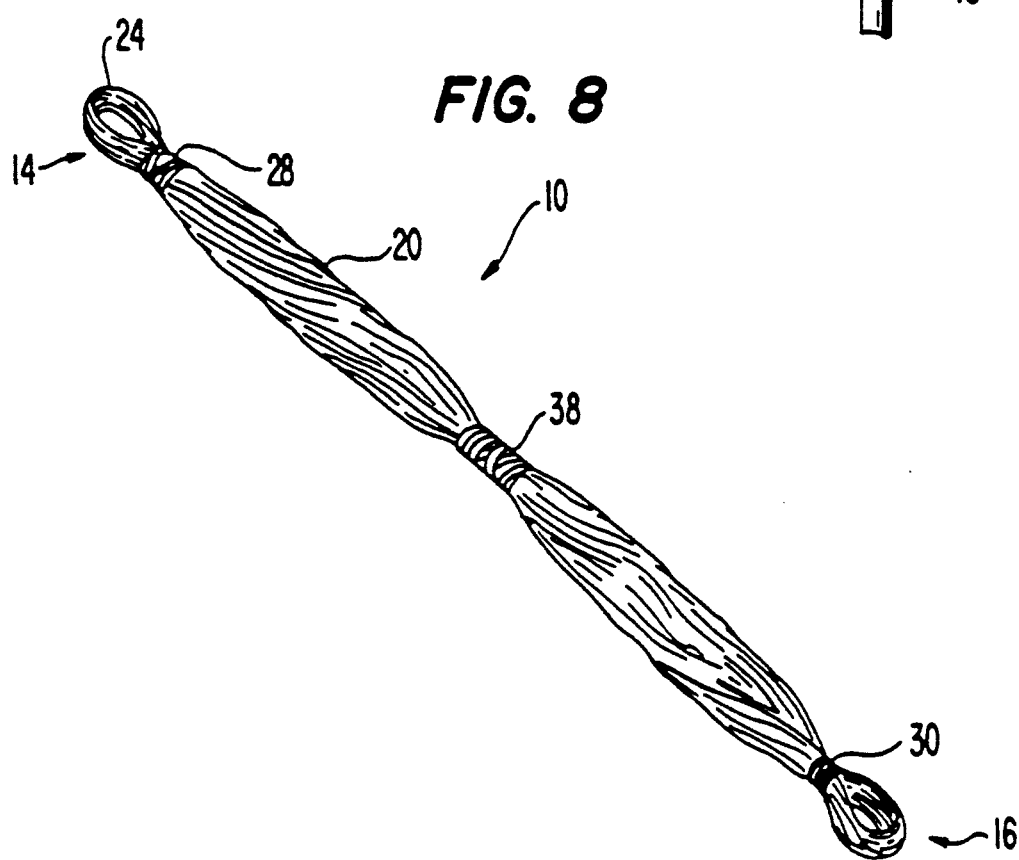
FIG. 8 shows a schematic perspective view of another prosthesis constructed in accordance with the present invention.
Figure 9:
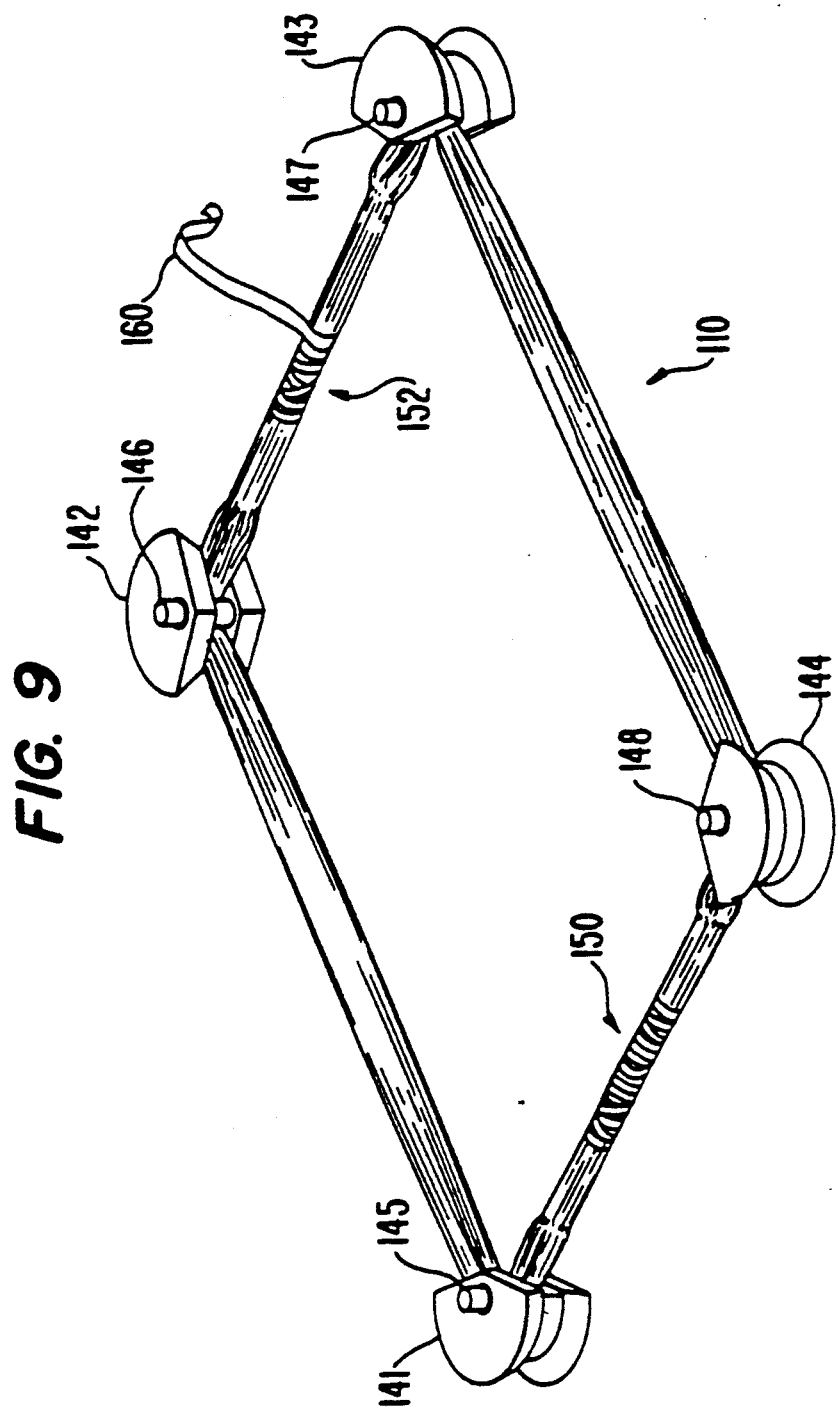
FIG. 9 depicts schematically a stage in another method of construction of a prosthesis of the present invention.

The bundle of strands was wrapped with this thin film at two points 28, 30 adjacent to the spools 42, 44, thereby forming eyelets 24, 26, at the ends of the construction (FIG. 8). A central portion 38 was also wrapped with film. The two spools were then demounted from the studs and placed on a rack constructed of thin metal wire designed to prevent rotation and longitudinal shrinkage. This rack was then exposed to 375° C. in an air oven for six minutes. After cooling, the spools were demounted from the ends of the construction. The position occupied by the spools provided eyelets through which this ligament prosthesis construction can be attached to bone with screws or other suitable means of fixation. All areas which had been wrapped with film had become compressed during the heating treatment due to film shrinkage, thereby providing strand-to-strand cohesion. During the previously described heating cycle, some fiber-to-fiber attachment in the unwrapped regions also took place. These fibers were then individually separated using a metal pick. The construction then comprised 160 microporous PTFE strands connecting two eyelets of somewhat densified material. Prosthesis 10 included a 180° twist along the tensile load direction to better distribute the tensile load among strands 20. PTFE tape wrap 38 surrounding strands 20 and positioned approximately midway between ends 14, 16 of prosthesis 10 serves to maintain the twist by securing strands 20 against untwisting during implantation. As with PTFE wraps 28, 30, wrap 38 is intended to be positioned outside of the bone contact area so as not to inhibit tissue ingrowth into strands 20.

A device prepared in the manner just described was implanted into the knee of a sheep to replace the excised host anterior cruciate ligament (see FIGS. 11A, B and C). This implantation was accomplished through the placement of one ¼" drill hole in both the tibia and femur. The placement of the hole in the tibia was along the axis of the previously removed natural anterior cruciate and exited at the insertion site. The placement of the femoral drill hole began at the lateral distal femoral surface proximal to the femoral epicondyle. The tunnel was angled such that the exit hole was created just proximal to the lateral femoral condyle on the popliteal surface of the femur. The prosthesis 10 was routed from the femoral exit site through the intercondylar space, across the intra-articular space, and through the tibial tunnel. The eyelets 24, 26 and wrapped segments 28, 30 at the ends of the construction were positioned to be to the outside of the drilled bone tunnels. The placement of the wrapped segment 38 at the center region of the construction was in the intra-articular space. The prosthesis 10 was then anchored to bone with self-tapping orthopedic screws 32, 34 placed through the eyelets 24, 26. The knee joint was determined to be stable immediately after the operation.

After three months implant time, the knee was removed from the animal and drill holes placed in the tibia and femur into which clamps were mounted to provide for tensile testing along the axis of the ligament construction. After removal of muscle tissue and severing of al supporting collateral structures about the knee, the femur was distracted from the tibia at a constant rate of 500 mm per minute until failure. System failure took place at 642 lb. The failure took place in the ligament prosthesis at the eyelet secured to the femur. Rupture took place as the load exceeded the fixation provided by tissue ingrowth into the intra-osseous segments and was transferred to the fixation screw. Device failure was related to an unwinding of the strand material through the eyelet segments after several strands had failed. Histologic inspection of this sample showed tissue ingrowth among and into the strands. Tissue ingrowth had proceeded completely through the diameter of some strands. We anticipate that with longer implant times the majority of strands would have shown complete and thorough ingrowth.

What is claimed is:

1. Method for making a tensile load-bearing tissue prosthesis having a longitudinal axis parallel to a plurality of longitudinally adjacent strands connected to at least one eyelet for initially attaching the prosthesis to tensile force-applying bone tissue, the method comprising the steps of:

a. selecting a strand material capable of permitting tissue growth in and through the strand material;

b. arranging and spacing a plurality of pin means to define an elongated area in accordance with the desired size of the prosthesis;

c. forming a plurality of elongated loops around the plurality of pin means from a continuous filament of the selected strand material until a desired number of parallel strands is obtained; and d. gathering the loop ends at one end of the elongated area to form the at least one eyelet, said gathering step including the step of securing the gathered loop ends against ungathering.

2. Method as in claim 1 including the additional step of imparting a twist to the loops about the longitudinal axis of the prosthesis after said step of forming a plurality of elongated loops.

3. Method as in claim 2 wherein the loops are twisted about 180°.

4. Method as in claim 1 wherein said step of forming a plurality of elongated loops includes the step of loosely braiding the strand material.

5. Method for making a tensile load-bearing tissue prosthesis having a longitudinal axis parallel to a plurality of longitudinally adjacent strands connected to at least one eyelet for initially attaching the prosthesis to tensile force-applying bone tissue, the method comprising the steps of:
   a. arranging and spacing a plurality of pin means to define an elongated area in accordance with the desired size of the prosthesis;
   b. forming a plurality of elongated loops around the plurality of pin means form a continuous filament of the desired strand material until a desired number of parallel strands is obtained; and
   c. gathering the loop ends at one end of the elongated area to form the eyelet, said gathering step including the step of securing the gathered loop ends against ungathering;
wherein the securing against ungathering step includes the step of compressing and heating the gathered ends at a temperature and for a time sufficient to coalesce the loop ends.

6. Method as in claim 5 wherein said step of securing against ungathering also includes the preliminary step of wrapping strands of a high strength material about the gathered ends in a direction orthogonal to the prosthesis axis at a position adjacent to the eyelet.

7. Method as in claim 6 wherein the high strength material is expanded polytetrafluoroethylene having a matrix tensile strength of about 74,000 psi.

8. Method as in claim 5 wherein the gathered ends are compressed and heated in a die having the desired eyelet shape and dimensions.

9. Method as in claim 1 wherein said step of forming a plurality of elongated loops includes the step of imparting a twist to the continuous filament.

* * * * *